(12) United States Patent
Goralczyk et al.

(10) Patent No.: US 7,919,531 B2
(45) Date of Patent: Apr. 5, 2011

(54) 3,5-DIHYDROXY-2,4-CYCLOHEXADIENONES AND THEIR DERIVATIVES, DIETARY COMPOSITIONS AND FORTIFIED FOOD CONTAINING THEM AND THEIR USES

(75) Inventors: Regina Goralczyk, Grenzach-Wyhlen (DE); Ann Fowler, Rheinfelden (CH); Goede Schuler, Eimeldingen (DE); Antoine De Saizieu, Brunstatt (FR)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/301,339

(22) PCT Filed: May 24, 2007

(86) PCT No.: PCT/EP2007/004628
§ 371 (c)(1),
(2), (4) Date: Jun. 23, 2009

(87) PCT Pub. No.: WO2007/134868
PCT Pub. Date: Nov. 29, 2007

(65) Prior Publication Data
US 2009/0270513 A1     Oct. 29, 2009

(30) Foreign Application Priority Data
May 24, 2006 (EP) .................... 06010885

(51) Int. Cl.
*A61K 31/122* (2006.01)
(52) U.S. Cl. ...................................... 514/689
(58) Field of Classification Search .............. 514/689
See application file for complete search history.

(56) References Cited

U.S. PATENT DOCUMENTS

| 6,080,410 A | 6/2000 | Bewicke et al. |
| 2003/0096027 A1 | 5/2003 | Babish et al. |
| 2005/0042318 A1 | 2/2005 | Erdelmeier et al. |

FOREIGN PATENT DOCUMENTS

| EP | 0212623 | 3/1987 |
| EP | 1198995 | 4/2002 |

OTHER PUBLICATIONS

Schiller et al. Sedating effects of *Humulus lupulus* L. extracts. Phytomedicine, 2006, vol. 13, p. 535-541.*
International Search Report for PCT/EP2007/004628, mailed Apr. 29, 2008.
Written Opinion for PCT/EP2007/004628, mailed Apr. 29, 2008.
Zanoli et al., "New Insight in the Neuropharmacological Activity of *Humulus lupulus* L", Journal of Ethnopharmacology, Elsevier Scientific Publishers Ltd., IE, vol. 102, No. 1, Oct. 31, 2005, pp. 102-106, XP005091358.
Database WPI Section Ch, Week 200240, Derwent Publications Ltd., London, GB; AN 2002-367590, XP002387546 & JP 2002-058450 A (Nippon Bio Medical Kenkyusho) Feb. 26, 2002, cited in the application.
Moerman, "Native American Ethnobotany" 1998, Timber Press, XP002476017.

* cited by examiner

*Primary Examiner* — Sikarl A Witherspoon
(74) *Attorney, Agent, or Firm* — Nixon & Vanderhye P.C.

(57) ABSTRACT

The present invention refers especially to 3,5-dihydroxy-2,4-cyclohexadienones of the general formula (I) wherein $R^1$ and $R^2$ are independently from each other $C_{1-6}$-alkyl, $C_{2-6}$-alkenyl or x-oxo-$C_x$-alkyl with x being an integer from 1 to 6, preferably $R^1$ and $R^2$ are independently from each other $C_{2-6}$-alkenyl or y-oxo-$C_y$-alkyl with y being an integer from 2 to 5, and wherein $R^3$ and $R^4$ are independently from each other hydroxy, $C_{1-6}$-alkyl, $C_{2-6}$-alkenyl or x-oxo-$C_x$-alkyl with x being an integer from 1 to 6, preferably $R^3$ and $R^4$ are independently from each other hydroxy or y-oxo-$C_y$-alkyl with y being an integer from 2 to 5, for use as mood balancing agents and stress relievers, as well as to dietary compositions and fortified food/feed/beverages containing such 3,5-dihydroxy-2,4-cyclohexadienones of the general formula (I), and their uses.

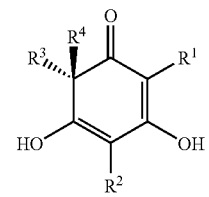

(I)

4 Claims, 3 Drawing Sheets

Fig. 3

3,5-DIHYDROXY-2,4-CYCLOHEXADIENONES AND THEIR DERIVATIVES, DIETARY COMPOSITIONS AND FORTIFIED FOOD CONTAINING THEM AND THEIR USES

This application is the U.S. national phase of International Application No. PCT/EP2007/004628, filed 24 May 2007, which designated the U.S. and claims priority to Europe Application No. 06010885.9 filed 24 May 2006, the entire contents of each of which are hereby incorporated by reference.

The present invention refers to 3,5-dihydroxy-2,4-cyclohexadienones of the general formula I as defined below for use as mood balancing agents and stress relievers, as well as to (dietary) compositions and fortified food/feed/beverages containing such 3,5-dihydroxy-2,4-cyclohexadienones of the general formula I, and their uses.

The present invention refers especially to humulone and lupulone, preferably to humulone, for use as mood balancing agents and stress relievers, as well as to (dietary) compositions and fortified food/feed/beverages containing them, and their uses. These two compounds (especially humulone) are preferably used for preventing stress in farm animals in mass production lifestock husbandry and/or during transport to slaughter and/or for preventing is quality loss of meat of said farm animals during transport to slaughter, for preventing feather picking and cannibalism amongst poultry, for reduction of stress in pet animals and for maintaining the circadian rhythm in humans, for alleviating and/or preventing the symptoms associated with a disturbed circadian rhythm in humans.

BACKGROUND AND SUMMARY

In few patent applications biological effects of humulone and/or lupulone have already been described which differ from the ones found by the inventors of the present invention.

DE 102 55 481 A1 e.g. discloses that hop extracts containing lupulone and/or humulone may prolong the sleeping time induced by narcotic agents such as ketamine hydrochloride. Thus, an effect of humulone and lupulone was shown in combination with another chemical substance such as ketamine hydrochloride.

US 2005/0042 318 describes an extract from hop having a content of bitter acids of at least 0.5%, of xanthohumol of at least 2%, and of prenylated flavones selected from the group comprising 6-prenylnaringenin, 8-prenylnaringenin and isoxanthohumol of at least 0.5%. This extract can be used for the prophylaxis and treatment of pathological conditions caused by oestrogen deficiency or by other hormone-related dysregulations (see US 2005/0042 318: page 2/3, [0019]; page 3, [0035]). Thus, it may be assumed that the extract has an oestrogenic effect (see example 5 of US 2005/0042 318). According to the tables of examples 1a, 1b, 2 and 3 the content of the α- and β-bitter acids of hop in the extract is low.

U.S. Pat. No. 6,080,410 describes the use of a dietary supplement in capsule form comprising ca. 150-250 mg pharmaceutical grade Kava root extract, ca. 25-100 mg passion flower, ca. 25-100 mg chamomile flowers; ca. 25-100 mg hops and ca. 25-100 mg Schizandra fruit for reducing daily stress and anxiety in adults. The composition of the hop extract used in this dietary supplement is not described nor the manufacture of the hop extract. Furthermore, an effect of a hop extract alone is not disclosed.

JP 2002-058 450 describes an antidepressant food product characterized in that it contains a powder or extract of at least one food material selected from the group a) spices mainly comprising hop extract, b) liquorice, c) Japanese angelica root, d) *Oenanthe javanica* root, and e) mushrooms, and has an antidepressant action against depression. According to Table 2 hops has an anti-depressant action, and the main components of hops are α-, β- and γ-humulone (bitter-tasting acids).

Imbalanced mood is connected to impaired neurotransmission, especially to impaired serotonin re-uptake, and increased susceptibility to stress.

Thus, mood is influenced by neurotransmitter biosynthesis, neurotransmitter processing, neurotransmitter storage, neurotransmitter release, neurotransmitter re-uptake and neurotransmitter receptor binding, especially wherein serotonin is the neurotransmitter. Imbalanced mood may manifest itself in animals including humans as tension, sadness, unhappiness/discontent, irritability and dysphoria, and/or as a disturbance of behaviour, emotions and thinking processes.

There is a need for compounds to stabilize mood and achieve emotional balance to cope with daily life stress and to maintain physical and psychological performance.

Mood disorders and occupational stress also lead to disturbances in circadian rhythms (so-called bio-rhythm). These conditions are often chronic and can persist over long time. Also, deregulation of circadian rhythms induced by long-term flights (jet-lag) as well as by shift-working can cause similar symptoms and distress. Therefore, treatment with dietary supplementation to maintain the normal circadian rhythm (an animal or human is used to), and/or to alleviate and prevent symptoms associated with a disturbed circadian rhythm such as impairment of cognitive function and memory, mental and physical fatigue is warranted to improve the overall quality of life and benefiting vital energy of a person in need thereof.

BRIEF DESCRIPTION OF THE FIGURES

FIG. 1 depicts structural formulas of lupulone as compound 1a and humulone as compound 2a;

DETAILED DESCRIPTION

According to the present invention this demand is met with 3,5-dihydroxy-2,4-cyclohexadienones of the general formula I, wherein $R^1$ and $R^2$ are independently from each other $C_{1-6}$-alkyl, $C_{2-6}$-alkenyl or x-oxo-$C_x$-alkyl with x being an integer from 1 to 6, preferably $R^1$ and $R^2$ are independently from each other $C_{2-6}$-alkenyl or y-oxo-$C_y$-alkyl with y being an integer from 2 to 5, and wherein $R^3$ and $R^4$ are independently from each other hydroxy, $C_{1-6}$-alkyl, $C_{2-6}$-alkenyl or x-oxo-$C_x$-alkyl with x being an integer from 1 to 6, preferably $R^3$ and $R^4$ are independently from each other hydroxy or y-oxo-$C_y$-alkyl with y being an integer from 2 to 5.

Figure 3:
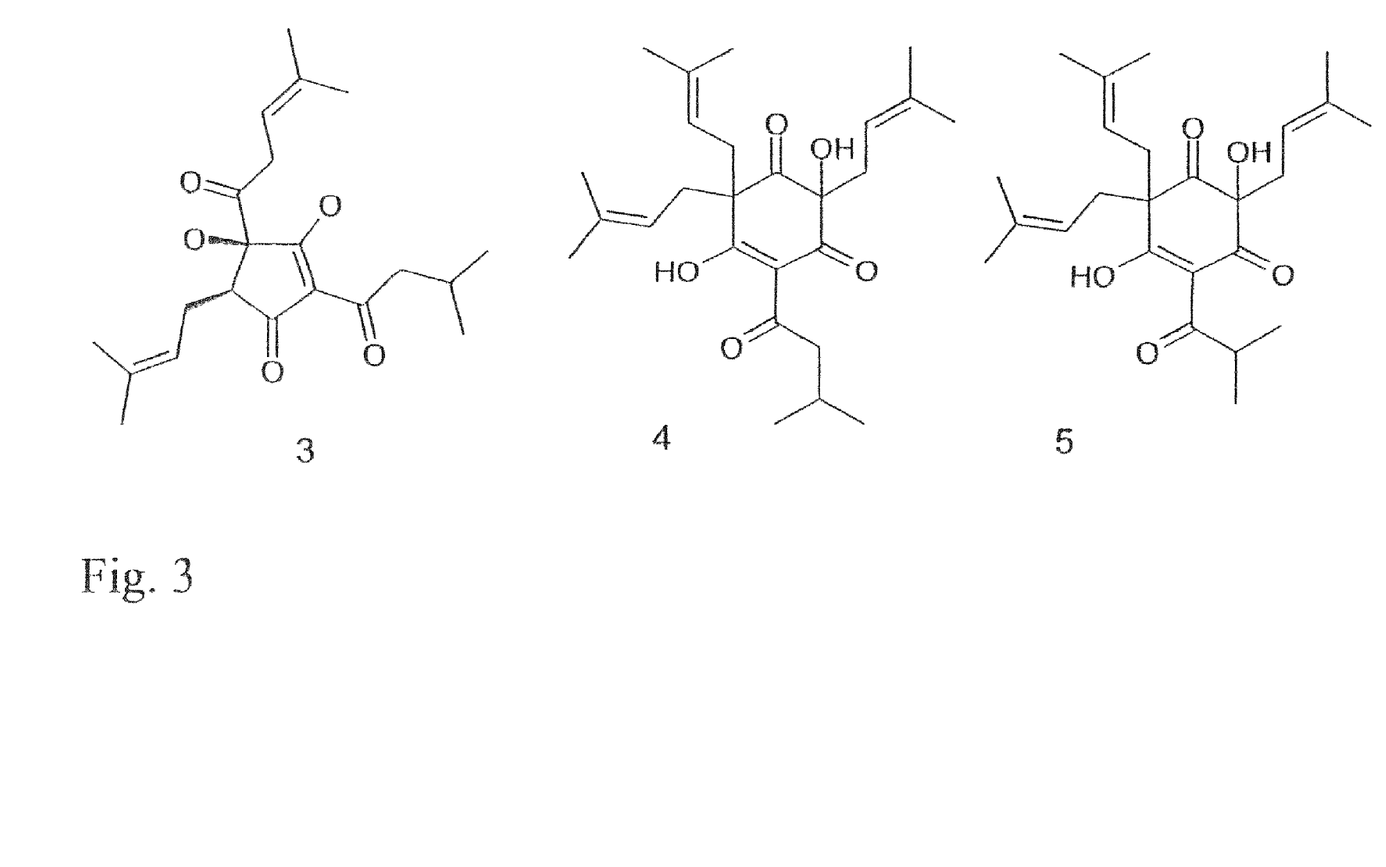
FIG. 3 depicts structural formulas of isohumulone as compound 3, 6-hydroxylupulone as compound 4 and 6-hydroxycolupulone as compound 5.

This result was especially astonishing since the structurally similar compounds 3 (isohumulone), 4 (6-hydroxylupulone) and 5 (6-hydroxycolupulone) (see FIG. 3) showed no effect in the experiments described below for serotonin re-uptake inhibition.

The 3,5-dihydroxy-2,4-cyclohexadienones of the general formula I as described above and with the preferences as described below act as serotonin re-uptake inhibitors, thus prolonging the time the serotonin is available for neurotransmission. This leads to a mood balancing and stress relieving effect.

The term "x-oxo-$C_x$-alkyl" means an alkyl group having x C atoms and containing an oxo-group. "1-oxo-$C_1$-alkyl" is e.g. formyl. An especially preferred example of x-oxo-$C_x$-alkyl is 1-oxo-3-methyl-butyl.

Preferred are 3,5-dihydroxy-2,4-cyclohexadienones of the general formula I, wherein $R^1$ and $R^2$ are independently from each other 1-oxo-3-methyl-butyl or isoprenyl and/or $R^3$ and $R^4$ are independently from each other hydroxy or isoprenyl.

Even more preferred are 3,5-dihydroxy-2,4-cyclohexadienones of the general formula I, wherein the 3,5-dihydroxy-2,4-cyclohexadienone of the general formula I is lupulone (compound 1, see FIG. 1) or humulone (compound 2, see FIG. 1), especially preferred is humulone, even more preferred is (−)-humulone.

The latter give positive results for inhibition of hSERT dependent uptake of tritiated serotonin into transfected cells.

The compound of the formula I encompasses all the following keto-enol-tautomers Ia to Ie:

Ia

Ib

Ic

Id

Ie

Figure 2:
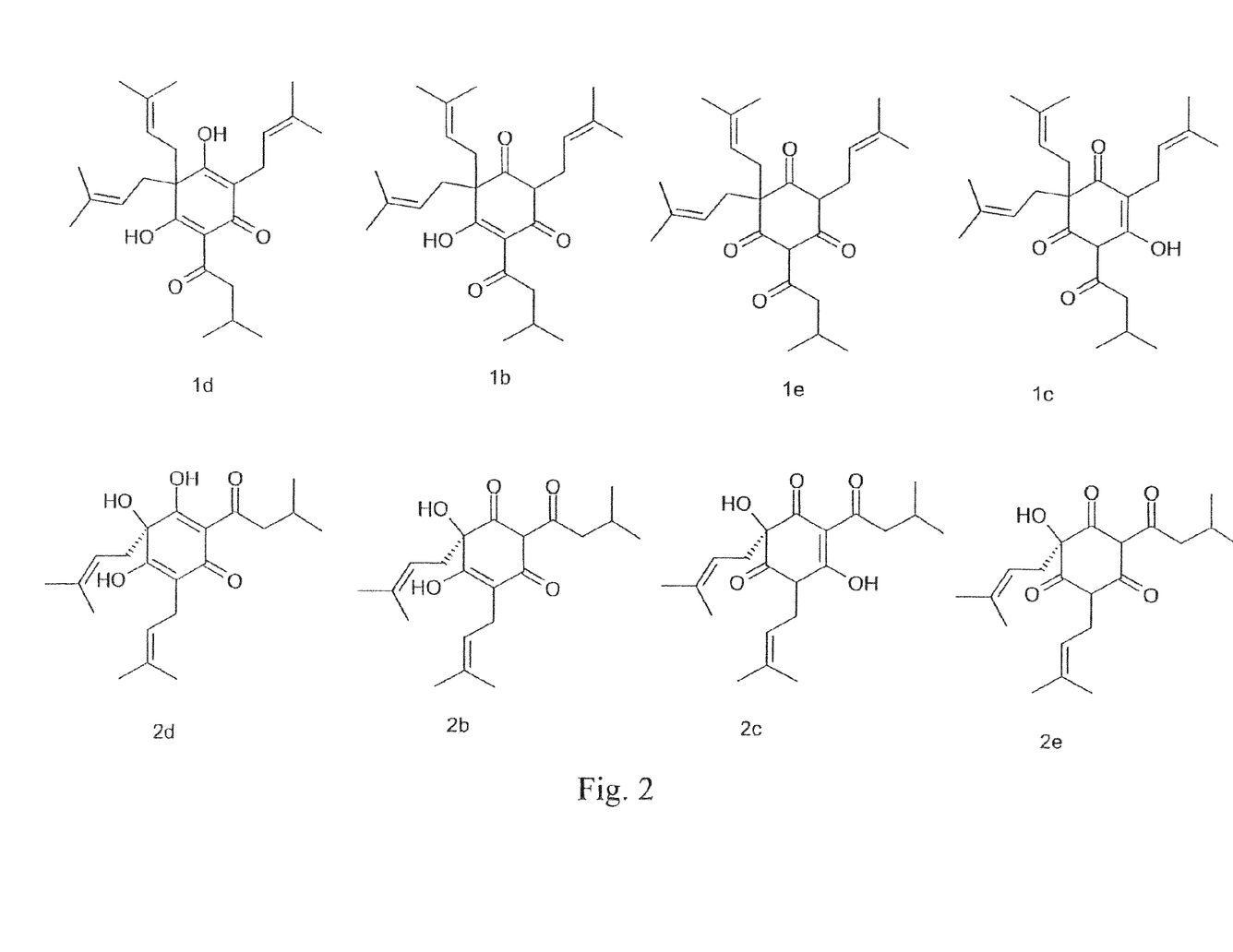
FIG. 2 depicts structural formulas of the keto-enol-tautomers of lupulone as compounds 1b-1e, and keto-enol-tautomers of humulone as compounds 2b-2e.

The same applies for humulone and lupulone (see FIG. 2).

Thus, in one aspect the invention relates to the use of a 3,5-dihydroxy-2,4-cyclohexadienone of the general formula I with the definitions of $R^1$ to $R^4$ as given above, preferably to lupulone and humulone, more preferably to humulone, most preferably to (−)-humulone, as mood balancing agent and/or stress reliever in animals including humans.

The animals are especially humans, pet animals (preferably cats and dogs), farm animals (preferably poultry, cattle, sheep, goat and swine) and animals for the fur industry such as minks, foxes and hares, as well as animals used for aquaculture such as fish like salmon and trout as well as crustaceous like shrimps.

In one preferred embodiment of the present invention the 3,5-dihydroxy-2,4-cyclohexadienone of the general formula I with the definitions of $R^1$ to $R^4$ as given above, preferably lupulone and humulone, more preferably humulone, most preferably (−)-humulone, are/is used for preventing stress in pet and farm animals, in mass production lifestock husbandry, during transport to slaughter and/or for preventing losses in milk or egg production, and quality loss of meat of said farm animals during transport to slaughter.

In another preferred embodiment of the present invention the 3,5-dihydroxy-2,4-cyclohexadienone of the general formula I with the definitions of $R^1$ to $R^4$ as given above, preferably lupulone and humulone, more preferably humulone, most preferably (−)-humulone, are/is used for preventing feather picking and cannibalism amongst poultry and/or for preventing losses of meat quality and egg production accompanied by it and in general.

In a further preferred embodiment of the present invention the 3,5-dihydroxy-2,4-cyclohexadienone of the general formula I with the definitions of $R^1$ to $R^4$ as given above, preferably lupulone and humulone, more preferably humulone, most preferably (−)-humulone, are/is used for maintaining the circadian rhythm in humans, for alleviating and/or for preventing the symptoms associated with a disturbed circadian rhythm in humans. Thus, mood is stabilized and an emotional balance is achieved to cope with daily life stress and to maintain physical and psychological performance. Furthermore, the symptoms associated with a disturbed circadian rhythm such as impairment of cognitive function and memory, mental and physical fatigue are alleviated and/or prevented so that the overall quality of life is improved and the persons to whom such compounds according to the present invention are administered benefit from maintaining vital energy. Also, deregulation of circadian rhythms induced by long-term flights (jet-lag) as well as by shift-working and the symptoms associated with it are alleviated and/or prevented.

Thus, imbalanced mood which may manifest as tension, sadness, unhappiness/discontent and irritability, dysphoria, and/or as a disturbance of behaviour, emotions and thinking processes, is prevented by administering the 3,5-dihydroxy-2,4-cyclohexadienone of the general formula I with the definitions of $R^1$ to $R^4$ as given above, preferably lupulone and humulone, more preferably humulone, to animals including humans.

In another aspect, the invention relates to the use of a 3,5-dihydroxy-2,4-cyclohexadienones of the general formula I as defined above (and with the preferences as given above) (for the manufacture of a composition) for use as a mood balancing agent, as a mood/vitality improver, as a stress reliever, as a condition improver, as a reducer of tension, sadness, unhappiness/discontent, irritability and dysphoria, as a reducer of obsessive-compulsive behaviour and/or as a relaxant.

In still another aspect, the invention relates to a composition containing at least one 3,5-dihydroxy-2,4-cyclohexadienones of the general formula I as defined above and with the preferences as given above. The present invention relates especially to a dietary composition containing at least one 3,5-dihydroxy-2,4-cyclohexadienones of the general formula I as defined above and with the preferences as given above; as well as to a pharmaceutical composition containing at least one 3,5-dihydroxy-2,4-cyclohexadienones of the general formula I as defined above and with the preferences as given above and a conventional pharmaceutical carrier.

Such a composition does essentially not contain an extract from the Kava-kava root.

In preferred embodiments of the present invention such a composition further does essentially not contain at least one compound selected from the group consisting of xanthohumol, 6-prenylnaringenine, 8-prenylnaringenine and isoxanthohumol.

More preferably such a composition does essentially not contain either of the following components: an extract from the Kava-kava root, xanthohumol, 6-prenylnaringenine, 8-prenylnaringenine and isoxanthohumol.

Even more preferably such a composition does essentially not contain either of the following components: an extract from the Kava-kava root, xanthohumol, 6-prenylnaringenine, 8-prenylnaringenine, and isoxanthohumol; and it does further essentially not contain at least one of the following components: (dried) passion flowers, (dried) chamomile flowers and Schizandra fruit (especially as described in U.S. Pat. No. 6,080,410 in column 3, line 44 to 60 and in column 4, line 1 to 5).

Most preferably such a composition does essentially not contain either of the following components: an extract from the Kava-kava root, xanthohumol, 6-prenylnaringenine, 8-prenylnaringenine, isoxanthohumol, (dried) passion flowers, (dried) chamomile flowers and Schizandra fruit.

"Essentially not containing" in the context of the present invention preferably means that no additional component as listed above (an extract from the Kava-kava root, xanthohumol, 6-prenylnaringenine, 8-prenylnaringenine, isoxanthohumol, (dried) passion flowers, (dried) chamomile flowers and Schizandra fruit) is added to the composition. It furthermore preferably means that if a hop extract or any other hop material as defined below having an amount of at least 50 weight-% of such a 3,5-dihydroxy-2,4-cyclohexadienones of the general formula I as defined above and with the preferences as given above is used, the amount of each of the following components: xanthohumol, 6-prenylnaringenine, 8-prenylnaringenine, isoxanthohumol is preferably below 0.5 weight-%, more preferably below 0.2 weight-%, even more preferably below 0.1 weight-%, based on the total weight of said hop extract or hop material. Most preferably the total amount of xanthohumol, 6-prenylnaringenine, 8-prenylnaringenine and isoxanthohumol together is $\leq 0.5$ weight-%, $\leq 0.2$ weight-%, $\leq 0.1$ weight-%, $\leq 0.05$ weight-%, based on the total weight of said hop extract or hop material.

Further, the invention relates to a method balancing the mood and/or relieving the stress in animals including humans, said method comprising administering an effective dose of a 3,5-dihydroxy-2,4-cyclohexadienone of the general formula I as defined above and with the preferences as given above to animals including humans which are in need thereof.

Animals in the context of the present invention include humans and encompass mammals, fish and birds. Preferred "animals" are humans, pet animals, farm animals, animals for the fur industry and in aquaculture.

Examples of pet animals are dogs, cats, birds, toy fish, guinea pigs, (jack) rabbits, hares and ferrets.

Examples of farm animals are fish (such as e.g. salmon and trout), aqua culture animals (such as e.g. shrimp), pigs, horses, ruminants (cattle, sheep and goat) and poultry (such as e.g. geese, chicken, broiler, laying hens, quails, ducks, turkeys).

Examples of animals for the fur industry are minks, foxes and hares.

In a preferred embodiment of the present invention the 3,5-dihydroxy-2,4-cyclohexadienone of the general formula I as defined above and with the preferences as given above is administered for preventing stress in farm animals, in mass production lifestock husbandry, during transport to slaughter and/or for preventing quality loss of meat of said farm animals during transport to slaughter. Said farm animals are especially poultry (such as e.g. geese, broiler, laying hens, quails, ducks, chicken, turkeys), cattle, sheep, goat and swine.

In another preferred embodiment of the present invention the 3,5-dihydroxy-2,4-cyclohexadienone of the general formula I as defined above and with the preferences as given above is administered to pet animals for reduction of stress, tension and aggressiveness and compulsive behavior under stressfully conditions such as separation, change or loss of the owner, during holiday separation and husbandry in so called "animal hotels", husbandry in animal shelter stations and other conditions of dense husbandry and breeding.

In another preferred embodiment of the present invention the 3,5-dihydroxy-2,4-cyclohexadienone of the general formula I as defined above and with the preferences as given above is administered to poultry (such as e.g. geese, broiler, laying hens, quails, ducks, chicken, turkeys) for preventing feather picking and cannibalism resulting e.g. in losses of meat quality and egg production.

In a further preferred embodiment of the present invention the 3,5-dihydroxy-2,4-cyclohexadienone of the general formula I as defined above and with the preferences as given above is administered to humans for maintaining the circadian rhythm in humans, for alleviating and/or preventing the symptoms associated with a disturbed circadian rhythm in humans.

Figure 1:
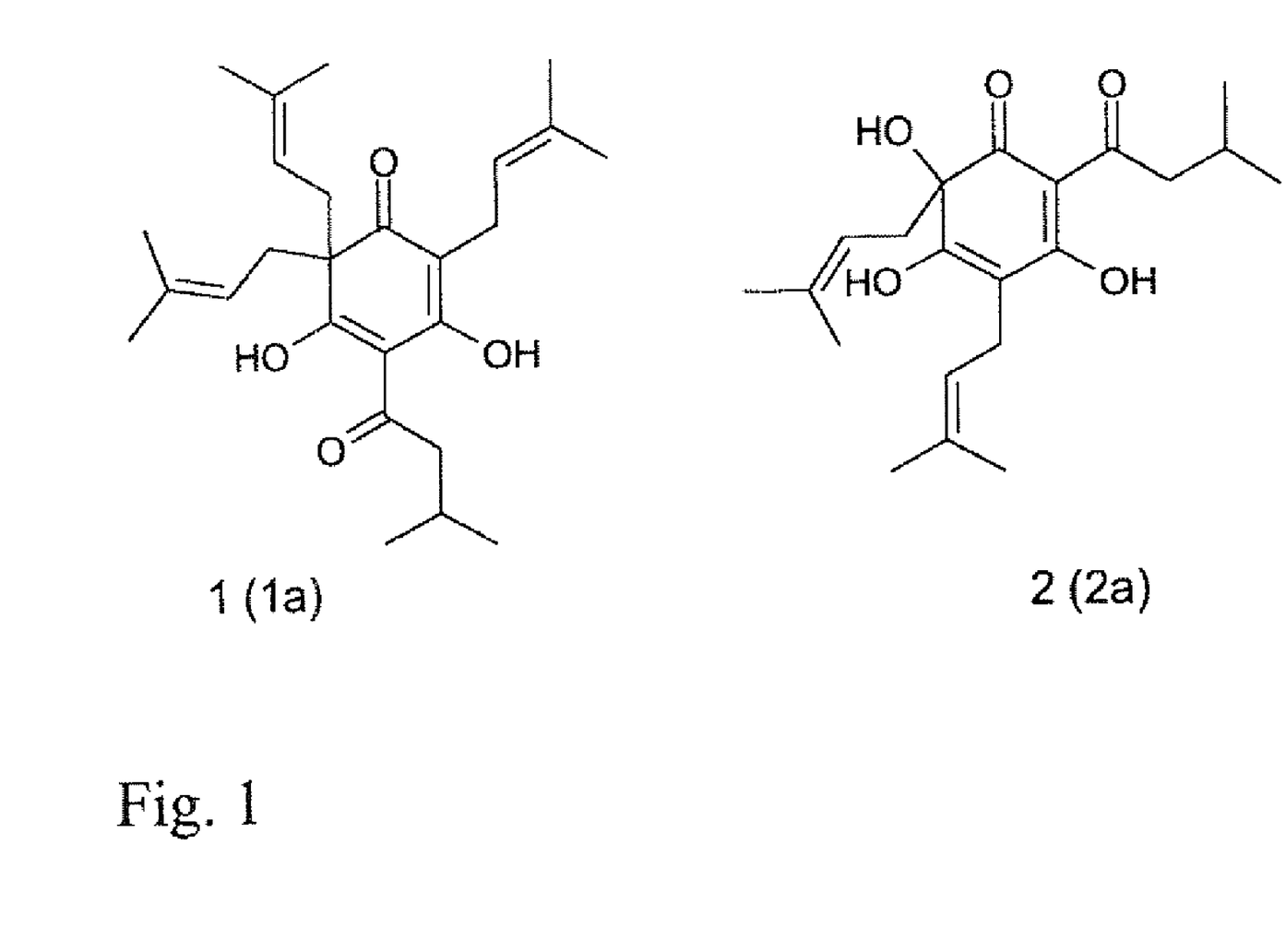

In a preferred aspect of the present invention the 3,5-dihydroxy-2,4-cyclohexadienones of the general formula I is selected from the group consisting of lupulone and humulone (compounds 1 and 2; see FIG. 1). Here the expression "compound 1" encompasses all keto-enol-tautomers as shown in FIG. 2. The same applies for the expression "compound 2" (see also FIG. 2).

More preferably the 3,5-dihydroxy-2,4-cyclohexadienones of the general formula I is (−)-humulone.

The term "3,5-dihydroxy-2,4-cyclohexadienone of the general formula I" also encompasses any material or extract of a plant containing such a 3,5-dihydroxy-2,4-cyclohexadienone of the general formula I in an amount of at least 50 weight-%, preferably in an amount of at least 70 weight-%, more preferably in an amount of from 70 to 90 weight-%, most preferably in an amount of at least 90 weight-%, based on the total weight of the plant material or extract. The terms "material of a plant" and "plant material" used in the context of the present invention mean any part of a plant. Such plant material or extract of a plant preferably does essentially not contain at least one compound selected from the group consisting of xanthohumol, 6-prenylnaringenine, 8-prenylnaringenine and isoxanthohumol. More preferably such plant material or extract of a plant does essentially not contain either of the following components: xanthohumol, 6-prenylnaringenine, 8-prenylnaringenine and isoxanthohumol.

"Humulone" means the racemic mixture as well as pure (−)-humulone or pure (+)-humulone or any mixture of them. Humulone, also called α-bitter acid or α-lupulic acid, can be isolated from plants like hops, but not limited to it.

Therefore, any material or extract of these plants or any other plant material or extract containing humulone in an amount of at least 50 weight-%, preferably in an amount of at least 70 weight-%, preferably in an amount of from 70 to 90 weight-%, more preferably in an amount of at least 90 weight-%, based on the total weight of the plant material or extract, is also encompassed by this expression. Such plant material or extract of a plant preferably does essentially not contain at least one compound selected from the group consisting of xanthohumol, 6-prenylnaringenine, 8-prenylnaringenine and isoxanthohumol. More preferably such plant material or extract of a plant does essentially not contain either of the following components: xanthohumol, 6-prenylnaringenine, 8-prenylnaringenine and isoxanthohumol. "Humulone" means both "natural" (isolated) and "synthetic" (manufactured) humulone.

Humulone's synthesis is described by Heitaro Obara, Junichi Onodera, Yoshihisa Machida and Shuji Yada in Bulletin of the Chemical Society of Japan 1989, 62(9), 3034-3035 ("A synthetic route to (±)-humulone").

Lupulone, also called β-bitter acid or β-lupulic acid, can be isolated from plants like hops, but not limited to it.

Therefore, any material or extract of these plants or any other plant material or extract containing lupulone in an amount of at least 50 weight-%, preferably in an amount of at least 70 weight-%, preferably in an amount of from 70 to 90 weight-%, more preferably in an amount of at least 90 weight-%, based on the total weight of the plant material or extract, is also encompassed by this expression. Such plant material or extract of a plant preferably does essentially not contain at least one compound selected from the group consisting of xanthohumol, 6-prenylnaringenine, 8-prenylnaringenine and isoxanthohumol. More preferably such plant material or extract of a plant does essentially not contain either of the following components: xanthohumol, 6-prenylnaringenine, 8-prenylnaringenine and isoxanthohumol. "Lupulone" means both "natural" (isolated) and "synthetic" (manufactured) lupulone.

Lupulone's synthesis is described by Shigeyuki Mizobuchi and Yuko Sato in Agricultural and Biological Chemistry 1985, 49(2), 399-403 ("Antifungal activities of hop bitter resins and related compounds").

Beside the (pure) compounds humulone and lupulone especially preferred are plant materials and plant extracts containing at least 50 weight-%, preferably at least 70 weight-%, more preferably from 70 to 90 weight-%, most preferably at least 90 weight-%, of these compounds, based on the total weight of the plant material/extract. These plant materials or plant extracts preferably do essentially not contain at least one compound selected from the group consisting of xanthohumol, 6-prenylnaringenine, 8-prenylnaringenine and isoxanthohumol. More preferably such plant materials or plant extracts do essentially not contain either of the following components: xanthohumol, 6-prenylnaringenine, 8-prenylnaringenine and isoxanthohumol.

According to the present invention not only the 3,5-dihydroxy-2,4-cyclohexadienones of the general formula I with the definitions of $R^1$ to $R^4$ and the preferences as given above, but also plant materials and extracts containing them in an amount of at least 50 weight-%, preferably in an amount of at least 70 weight-%, more preferably in an amount of from 70 to 90 weight-%, most preferably in an amount of at least 90 weight-%, based on the total weight of the plant material or extract, as well as compositions, especially dietary and to pharmaceutical compositions, containing them can be used according to the present invention, i.e. for the purposes and in the methods as described above.

The dietary compositions according to the present invention may further contain protective hydrocolloids, binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellyfying agents, gel forming agents, antioxidants and antimicrobials.

The term "dietary compositions" comprises any type of clinical nutrition and dietary supplements.

Beside a pharmaceutically acceptable carrier and at least one 3,5-dihydroxy-2,4-cyclohexadienone of the general formula I with the definitions of $R^1$ to $R^4$ and the preferences as given above, the pharmaceutical compositions according to the present invention may further contain conventional pharmaceutical additives and adjuvants, excipients or diluents, including, but not limited to, water, gelatin of any origin, vegetable gums, lignin-sulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like. The carrier material can be organic or inorganic inert carrier material suitable for oral/parenteral/injectable administration.

The dietary and pharmaceutical compositions according to the present invention may be in any galenic form that is suitable for administration to the animal body including the human body, especially in any form that is conventional for oral administration, e.g. in solid form such as additives/supplements for food or feed, food or feed premix, fortified food or feed, tablets, pills, granules, dragées, capsules, and effervescent formulations such as powders and tablets, or in liquid form such as solutions, emulsions or suspensions as e.g. beverages, pastes and oily suspensions. The pastes may be filled into hard or soft shell capsules. Examples for other application forms are forms for transdermal, parenteral or injectable administration. The dietary and pharmaceutical compositions may be in the form of controlled (delayed) release formulations.

The composition of the present invention is preferably in form of nutrition such as fortified food, fortified feed, fortified beverages, or in form of fortified liquid food/feed for animals including humans.

"Fortification" means that at least one 3,5-dihydroxy-2,4-cyclohexadienone of the general formula I as defined above and with the preferences as given above was added during manufacture or consumption of said food/feed or beverage.

Examples for food are dairy products such as yoghurts, cereal bars, bakery items such as cakes and cookies.

Beverages encompass non-alcoholic and alcoholic drinks as well as liquid preparations to be added to drinking water and liquid food. Non-alcoholic drinks are e.g. soft drinks, sport drinks, fruit juices, lemonades, near-water drinks (i.e. water based drinks with a low calorie content), teas and milk based drinks. Liquid food are e.g. soups and dairy products (e.g. muesli drinks).

Feed encompasses any feed given to pet animals, farm animals, animals for the fur industry and aquaculture animals. It also encompasses treats given to pet animals (such as e.g. dogs and cats).

The composition of the present invention is, thus, especially in form of food such as dairy products (yoghurts), in form of fortified food such as cereal bars and bakery items such as cakes and cookies, in form of dietary supplements such as tablets, pills, granules, dragées, capsules, and effervescent formulations, in form of non-alcoholic drinks such as soft drinks, sport drinks, fruit juices, lemonades, teas and milk based drinks, in form of liquid food such as soups and dairy products (muesli drinks).

Thus, the 3,5-dihydroxy-2,4-cyclohexadienones of the general formula I with the definitions of $R^1$ to $R^4$ and the preferences as given above can be used for the manufacture of compositions for use as mood balancing agent, as mood/vitality improver, as stress reliever, as condition improver, as reducer of tension, sadness, unhappiness/discontent, irritability and dysphoria, as reducer of obsessive-compulsive behaviour and/or as relaxant.

In the context of this invention "prevention" can be the prevention of the first occurrence (primary prevention) or the prevention of a reoccurence (secondary prevention). The term "prevention" also encompasses the reduction of the risk or incidence of developing certain symptoms, e.g. associated with a disturbed circadian rhythm.

Thus, the present invention is also directed to a method for maintaining the mental well-being, for maintaining a balanced cognitive function, for helping to reduce the risk of mood swings, for helping to retain a positive mood and for supporting cognitive wellness in animals including humans, said method comprising administering an effective dose of a 3,5-dihydroxy-2,4-cyclohexadienone of the general formula I with the definitions of $R^1$ to $R^4$ and the preferences as given above to animals including humans which are in need thereof.

Thus, the 3,5-dihydroxy-2,4-cyclohexadienone of the general formula I with the definitions of $R^1$ to $R^4$ and the preferences as given above act as mood balancing agents, as mood/vitality improvers, stress relievers, condition improvers, tension reducers, sadness reducers, unhappiness/discontent and irritability reducers, dysphoria reducers and obsessive-compulsive behaviour reducers and/or relaxants. They all may improve, enhance and support the physiological neurotransmission, especially in the central nervous system, and therefore may alleviate mental malfunction.

The 3,5-dihydroxy-2,4-cyclohexadienones of the general formula I with the definitions of $R^1$ to $R^4$ and the preferences as given above as well as (mixtures of) plant materials and plant extracts (essentially) containing them in an amount of at least 50 weight-%, preferably in an amount of at least 70 weight-%, more preferably in an amount of from 70 to 90 weight-%, most preferably in an amount of at least 90 weight-%, based on the total weight of the plant material or extract, and dietary/pharmaceutical compositions containing them are thus suitable for the treatment of animals including humans.

Especially pet animals and farm animals can be in conditions in need of enhanced or improved neurotransmission. Such conditions e.g. occur after capture or transport or with housing, when the animals develop analogous disorders and are distressed or aggressive, or display stereotypic behaviour, or tension, sadness, unhappiness/discontent and irritability, dysphoria and obsessive-compulsive behaviour.

Thus, the 3,5-dihydroxy-2,4-cyclohexadienones of the general formula I with the definitions of $R^1$ to $R^4$ and the preferences as given above can be used in general as mood balancing agents and/or stress relievers for animals including humans, preferably for humans, pet animals and farm animals.

In a further embodiment of the present invention the 3,5-dihydroxy-2,4-cyclohexadienones of the general formula I with the definitions of $R^1$ to $R^4$ and the preferences as given above find use as mood improver in general as well as for the manufacture of compositions for such use (plant materials/extracts; dietary/pharmaceutical compositions). "Mood improver" or "emotional wellness booster" or "vitality improver" means that the mood of a person treated with it is enhanced, that the self esteem is increased and/or that negative thoughts and/or negative tension, sadness, unhappiness/discontent and irritability, and dysphoria are/is reduced. It also means the emotions are balanced and/or that the general, especially the mental, well being and vitality is improved or maintained, as well as that the risk of mood swings is (helped to be) reduced and that the positive mood is (helped to be) retained.

The 3,5-dihydroxy-2,4-cyclohexadienones of the general formula I with the definitions of $R^1$ to $R^4$ and the preferences as given above can also be used in general as tension reducer, sadness reducer, unhappiness/discontent and irritability reducer, dysphoria reducer and/or obsessive-compulsive behaviour reducer for animals including humans, preferably for pet animals and farm animals.

"Tension reducer, sadness reducer, unhappiness/discontent and irritability reducer, dysphoria reducer" means that (chronic) tension and worrying are alleviated and relieved. Hypervigilance syndrome, including restlessness and muscle tension are relieved. Social and other phobias are resolved. In general, the social environment is experienced less threatening. The person is emotionally relaxed, experiences comfort and enjoys company and contact to other people.

"Relaxant" means to correct circadian rhythm associated disturbances due to jet-lag or shift work, and to prevent and abolish the symptoms associated with it, i.e. impairment of cognitive function and memory, mental and physical fatigue, and improve overall quality of life and vital energy. Thus, the 3,5-dihydroxy-2,4-cyclohexadienones of the general formula I with the definitions of $R^1$ to $R^4$ and the preferences as given above may also be used to prevent and/or abolish the impairment of cognitive function and memory, to prevent and/or abolish mental and physical fatigue, and to improve overall quality of life and vital energy.

Moreover, 3,5-dihydroxy-2,4-cyclohexadienones of the general formula I with the definitions of $R^1$ to $R^4$ and the preferences as given above as well as compositions comprising an effective dose of them are useful for the treatment, prevention and the alleviation of stress related symptoms, for the treatment, prevention and alleviation of symptoms related to working overload, exhaustion and/or burn out, for the increase of the resistance or tolerance to stress and/or to favor and facilitate the relaxation in normal healthy individuals i.e. such compositions have an effect as "stress reliever".

Furthermore, 3,5-dihydroxy-2,4-cyclohexadienones of the general formula I with the definitions of $R^1$ to $R^4$ and the preferences as given above as well as compositions comprising an effective dose of them are useful for the treatment, prevention and alleviation of tension, sadness, unhappiness/discontent and irritability, dysphoria and obsessive-compulsive behaviour in humans and animals.

A further embodiment of the present invention relates to the use of 3,5-dihydroxy-2,4-cyclohexadienones of the general formula I with the definitions of $R^1$ to $R^4$ and the preferences as given above and to the use of compositions containing them (plant materials/extracts; dietary/pharmaceutical compositions) as "condition improver", i.e. as means to reduce irritability and tiredness, to reduce or prevent or alleviate physical and mental fatigue, and to increase energy in more general terms, especially to increase the brain energy production, in diseased or normal healthy individuals. Moreover for cognition improvement in general, and especially for maintenance or improvement of attention and concentration, of the memory and of the capacity for remembering, of the learning ability, of the language processing, of problem solving and of intellectual functioning; for improvement of the short-term memory; for increasing the mental alertness; for enhancing the mental vigilance; for reducing the mental fatigue; for supporting cognitive wellness, for maintaining balanced cognitive function, for the regulation of hunger and satiety as well as for the regulation of motor activity.

The present invention not only refers to 3,5-dihydroxy-2,4-cyclohexadienones of the general formula I with the definitions of $R^1$ to $R^4$ and the preferences as given above and their compositions (i.e. (mixture(s) of) plant extracts (essentially) containing them; dietary/pharmaceutical compositions containing them) for use as mood balancing agents, as mood/vitality improvers, as stress relievers, as condition improvers, as reducers of anxiety, as reducers of obsessive-compulsive behaviour and/or as relaxants, but also for the methods for the treatment of such disturbances themselves, as already mentioned above.

In an especially preferred embodiment of such method pet animals or farm animals whose disorders are associated with housing, capture or transport are treated and which may appear in form of anxiety, aggressiveness or obsessive-compulsive behavior. The 3,5-dihydroxy-2,4-cyclohexadienone of the general formula I with the definitions of $R^1$ to $R^4$ and the preferences as given above is in that case preferably administered as fortified feed or fortified beverage (e.g as addition to the drinking water).

For humans a suitable daily dosage of a 3,5-dihydroxy-2,4-cyclohexadienone of the general formula I with the definitions of $R^1$ to $R^4$ and the preferences as given above, for the purposes of the present invention may be within the range from 0.001 mg per kg body weight to about 20 mg per kg body weight per day. More preferred is a daily dosage of about 0.01 to about 10 mg per kg body weight, and especially preferred is a daily dosage of about 0.05 to 5.0 mg per kg body weight. The amount of a plant material or plant extract containing such 3,5-dihydroxy-2,4-cyclohexadienone of the general formula I can be calculated accordingly.

In solid dosage unit preparations for humans, the 3,5-dihydroxy-2,4-cyclohexadienone of the general formula I with the definitions of $R^1$ to $R^4$ and the preferences as given above, is suitably present in an amount from about 0.1 mg to about 1000 mg, preferably from about 1 mg to about 500 mg per dosage unit. For relieve of symptoms associated with conditions as defined above, the compound is taken once or twice per day together with a meal for at least one week up to 6-12 months. For prevention of occurrence of symptoms associated with conditions as defined above, and for the maintenance of a generally relaxed state, consumption on a regular basis is suitable.

In dietary compositions, especially in food and beverages for humans, the 3,5-dihydroxy-2,4-cyclohexadienone of the general formula I with the definitions of $R^1$ to $R^4$ and the preferences as given above, is suitably present in an amount of from about 0.0001 (1 mg/kg) to about 5 weight-% (50 g/kg), preferably from about 0.001% (10 mg/kg) to about 1 weight-%, (10 g/kg) more preferably from about 0.01 (100 mg/kg) to about 0.5 weight-% (5 g/kg), based upon the total weight of the food or beverage. For relieve of symptoms associated with conditions as defined above, the food product is taken once or twice per day at least for one to three weeks or on a regular basis once daily.

In food and drinks in a preferred embodiment of the invention the amount of the 3,5-dihydroxy-2,4-cyclohexadienone of the general formula I with the definitions of $R^1$ to $R^4$ is 10 to 30 mg per serving, i.e. 120 mg per kg food or drink. The food product is taken once or twice per day at least for one to three weeks or on a regular basis once daily.

For animals excluding humans a suitable daily dosage of the 3,5-dihydroxy-2,4-cyclohexadienone of the general formula I with the definitions of $R^1$ to $R^4$ and the preferences as given above, for the purposes of the present invention may be within the range from 0.001 mg per kg body weight to about 1000 mg per kg body weight per day. More preferred is a daily dosage of about 0.1 mg to about 500 mg per kg body weight, and especially preferred is a daily dosage of about 1 mg to 100 mg per kg body weight. To prevent and reduce symptoms associated with stressful conditions, such as mass production lifestock husbandry and fur industry husbandry or aquaculture, the product is given over the entire lifetime until slaughter. Especially in the case, where farm animals such as poultry, cattle, sheep, goat and swine, especially cattle and swine, are transported to get slaughtered, they get a daily dosage of 100-200 mg/kg body weight preferably during transportation, more preferably at least 3 days before transportation and during transportation. For pets, under stressful conditions as in animal shelter farms or pet shops, the product shall be given at least for 1-3 weeks or over the whole husbandry period. Under conditions of short-term stress, such as holiday separation, husbandry in animal "holiday hotels", visit or stays in veterinarian clinics, the product may be given at minimum 3 days, better 7 days before the stressful event.

The invention is illustrated further by the following examples.

EXAMPLES

In the examples (−)-humulone obtained from Apin Chemicals Ltd. (Abingdon, United Kingdom) was used. It had a purity of ≧90%. (The (−)-humulone used in examples 3 and 4 had a purity of 94.5%. The (−)-humulone used in example 5 had a purity of 93.1%.)

In the examples lupulone obtained from Apin Chemicals Ltd. (Abingdon, United Kingdom) was used. It had a purity of ≧90%.

Example 1

Serotonin Uptake Inhibition by (−)-Humulone and Lupulone

HEK-293 cells stably expressing the human serotonin re-uptake transporter (hSERT) were obtained from R. Blakely, Vanderbilt University, USA. The cells were routinely grown in Dulbeco's Modified Eagles Medium (Bioconcept) containing 10% fetal calf serum, penicillin, streptomycin, L-glutamine and the antibiotic G418 and passaged by trypsinisation. On the day of assay, cells from 80% confluent flasks were harvested by gentle washing with warm phosphate buffered saline (PBS). Cells were then washed once by centrifugation and re-suspended in Krebs Ringers bicarbonate buffer (Sigma) supplemented with 35 µM pargyline, 2.2 mM $CaCl_2$, 1 mM ascorbic acid and 5 mM N-2-hydroxyethylpiperazine-N'-2-ethanesulfonic acid (buffer called "Hepes") at a concentration of 10,000 cells in 160 ul of buffer, and aliquoted into round bottomed polypropylene 96 well microtitre plates (Corning) at 10,000 cells per well. Serotonin uptake into the cells was determined by addition of radiolabeled (3H) serotonin (GE Healthcare) to a concentration of 20 nM, and incubation for 40 minutes at 37° C. with gentle shaking. At the end of this time unincorporated label was removed by filtration though Unifilter 96 GF/B plates (Perkin Elmer) using a Tomtec Mach III M cell harvester. The incorporated serotonin retained on the plates was quantified by liquid scintillation counting using Microscint-40/Topcount (Perkin Elmer).

The effect of (−)-humulone and lupulone on the serotonin uptake was determined by their inclusion in the assay at a range of concentrations between 0.03 and 100 µM for 10 minutes prior to and during the addition of (3H) serotonin. Serotonin uptake via the transporter was inhibited by (−)-humulone and lupulone, respectively, in a dose dependent manner.

The calculated inhibition constants $K_i$, derived from the measured IC50 using the Cheng-Prusoff equation (Y. C. Cheng, W. H. Prusoff, Biochem. Pharmacol. 1973, 22, p. 3099-3108), for inhibition of serotonin uptake by (−)-humulone and lupulone are shown in Table 1.

TABLE 1

Inhibition constants for inhibition of serotonin uptake into transfected HEK-293 cells by (−)-humulone and lupulone

| Substance | Inhibition constant $K_i$ [µM] for tritiated serotonin uptake |
|---|---|
| Humulone | 16.9 +/− 3.8 |
| Lupulone | 6.0 +/− 0.3 |

Since the experiments were carried out twice the average value +/− the standard error in the mean (s.e.m.) is shown.

Example 2

Effect of (−)-Humulone in the Primary Observation (Irwin) Test in the Mouse

The method, which detects the first toxic dose, the active dose-range and the principal effects of a test substance on behaviour and physiological function, follows that described by Irwin (Irwin S. Comprehensive observational assessment: A systematic quantitative procedure for assessing the behavioural and physiologic state of the mouse. Psychopharmacologia, 1968, 13, 222-257).

Mice were administered the test substance ((−)-humulone) and were observed in simultaneous comparison with a control group given vehicle (non-blind conditions). 3 treated groups were compared with the same control at any one time. All animals within a treatment group were observed simultaneously.

Behavioural modifications, physiological and neurotoxicity symptoms, pupil diameter and rectal temperature were recorded according to a standardized observation grid derived from that of Irwin. The grid contains the following items: lethality*, convulsions*, tremor*, Straub*, sedation, excitation, abnormal gait* (rolling, tip-toe), jumps*, motor incoordination*, writhes*, piloerection*, stereotypies* (sniffing, chewing, head movements), head twitches*, scratching*, respiration*, aggressiveness*, fear, reactivity to touch, muscle tone, loss of righting reflex, ptosis, exopthalmos, loss of grasping, akinesia, catalepsy, loss of traction, loss of corneal reflex, analgesia, defecation, salivation, lacrimation, pupil diameter (Unit=1/45 mm) and rectal temperature.

Observations were performed 15, 30, 60, 120 and 180 minutes after administration of the test substance ((−)-humulone) and also 24 hours later. The symptoms marked (*) were observed continuously from 0 to 15 minutes after administration. 5 mice were studied per group.

(−)-Humulone was solubilized in physiological saline and injected into mice intraperitoneally.

Results

At 10 mg/kg, (−)-humulone had no observable effects.

At 30 mg/kg, it decreased fear in 3 mice at 30 minutes and in 1 mouse at 60 minutes and decreased muscle tone in 4 mice at 30 minutes and in 1 mouse at 60 minutes.

Overall, this results indicates that (−)-humulone decreased fear and cause a slight relaxant effect.

Example 3

Marble Burying Test

"Defensive burying" behaviour was demonstrated by rats burying noxious objects, such as drinking spouts filled with a unpleasant-tasting liquid (WILKIE, D. M., MACLENNAN, A. J. & PINEL, J. P. J. (1979). Rat defensive behavior: burying noxious food. Journal of the Experimental Analysis of Behavior, 31, 299-306.) or shock prods (PINEL, J. P. J. & TREIT, D. (1978). Burying as a defensive response in rats. Journal of Comparative and Physiological Psychology, 92, 708-712.). The marble burying test was devised as a modification of such a test. Poling et al. (POLING, A., CLEARY, J. & MONAGHAN, M. (1981). Burying by rats in response to aversive and nonaversive stimuli. Journal of the Experimental Analysis of Behavior, 35, 31-44.) exposed rats to individual cages each containing 25 marbles, daily for 10 or 21 consecutive days. The number of marbles buried, on each day of the day (d) period, or 24 hours (h) after the 21 d exposure, were counted. The authors reported that the burying of marbles was not determined by novelty, or due to any noxious stimuli.

Marble burying behaviour by mice is reported to be sensitive to a range of minor (e.g. diazepam) and major (e.g. haloperidol) tranquilisers (BROEKKAMP, C. L., RIJK, H. W., JOLY-GELOUIN, D. & LLOYD, K. L. (1986). Major tranquillizers can be distinguished from minor tranquillizers on the basis of effects on marble burying and swim-induced grooming in mice. European Journal of Pharmacology, 126, 223-229.), in addition to SSRIs (e.g. fluvoxamine, fluoxetine, citalopram), tricyclic antidepressants (e.g. imipramine, desipramine) and selective noradrenaline uptake inhibitors (e.g. reboxetine), at doses which do not induce sedation. The model may reflect either anxiety-like- or obsessive-compulsive-behaviour (see DE BOER, S. F. & KOOLHAAS, J. M.

(2003). Defensive burying in rodents: ethology, neurobiology and psychopharmacology. European Journal of Pharmacology, 463, 145-161.).

The method applied here follows that described by Broekkamp et al. (European Journal of Pharmacology 1986, 126, 223-229.). Mice (n=15 per treatment group) were individually placed in transparent plastic cages (33×21×18 cm) with 5 cm of sawdust on the floor and 25 marbles (diameter 1 cm) grouped in the centre of the cage. A second, up-turned, cage served as a lid. The number of marbles covered by sawdust (by at least two-thirds) was counted at the end of the 30-minute test period. Tests were performed by investigators blind to the drug treatment protocol.

Prior to testing, all test cages and marbles were "impregnated" by leaving 10 naive mice in each cage for 15 minutes.

(−)-Humulone was solubilized in physiological saline. The control substance fluoxetine (Prozac®) (Lilly), batches n° A069667 and A058238) was dispersed in 0.2% hydroxypropylmethylcellulose (HPMC) in physiological saline.

(−)-Humulone was evaluated at 3, 10 and 30 mg/kg, administered i.p. 30 minutes before the test, and compared with a vehicle control group. Fluoxetine (32 mg/kg), administered under the same experimental conditions, was used as a reference substance.

Data were analysed by comparing treated groups with vehicle control using unpaired Student's t-tests.

Results

TABLE 2

Effects of (−)-humulone and fluoxetine in the marble burying test in the mouse

| i.p. −30 min | (−)-humulone (mg/kg) NUMBER OF MARBLES COVERED BY SAWDUST | | |
|---|---|---|---|
| | mean ± s.e.m. | p value | % change from control |
| Vehicle | 20.1 ± 1.7 | — | — |
| 3 | 18.3 ± 1.7 (NS) | 0.4449 | −9% |
| 10 | 17.5 ± 2.0 (NS) | 0.3288 | −13% |
| 30 | 3.8 ± 1.5 (***) | <0.0001 | −81% |
| FLUOXETINE 32 mg/kg i.p. −30 min | 1.9 ± 1.0 (***) | <0.0001 | −91% |

Student's t test:
(NS) = Not Significant;
(***) = p < 0.001

The highest dose of (−)-humulone tested (30 mg/kg) clearly and significantly reduced marble burying behaviour, in a similar manner to the SSRI fluoxetine.

Example 4

Effect of (−)-Humulone in the Light Dark Box Test in the Mouse after Subchronic, Oral Gavage The method, which detects anxiolytic activity, follows that described by Crawley (*Pharmacol. Biochem. Behav.* 1981, 15, 695-699). Anxiolytics increase the time spent in the light compartment.

Animals were placed into the light compartment of a 2-compartment box with one half light and open (25×27×27 cm) and the other half dark and closed (20×27×27 cm). The time spent in each compartment as well as the number of times the animal crosses from one side to the other is scored during a 3-minute test. 15 mice were studied per group. The test was performed blind.

(−)-Humulone evaluated at 3 doses (50, 100, 200 mg/kg BW, solubilized in corn oil) was administered orally 3 times at 25, 5 and 1 hour before the test, and compared with a vehicle (corn oil) control group.

Clobazam (32 mg/kg orally), administered 1 hour before the test, will be used as reference substance. Mice in this group received additional administrations of vehicle at 25 and 5 hours before the test in order to maintain experimental blinding.

Results are shown in Table 3.

TABLE 3

| TREATMENT (mg/kg) p.o. -24 h, 5 h and 1 h before test | TIME SPENT IN LIGHT COMPARTMENT (s) | | | NUMBER OF CROSSINGS | | |
|---|---|---|---|---|---|---|
| | Mean ± sem | p-value | % change | Mean ± sem | P value | % change |
| Vehicle | 64.4 ± 4.7 | — | — | 6.5 ± 1.0 | — | — |
| (−)-humulone (50) | 95.4 ± 3.8 | <0.0001 | +48% | 13.7 ± 1.3 | <0.0001 | +111% |
| (−)-humulone (100) | 86.4 ± 8.9 | 0.0380 | +34% | 7.9 ± 1.0 | 0.2865 | +22% |
| (−)-humulone (200) | 71.5 ± 8.8 | 0.4611 | +11% | 8.3 ± 1.2 | 0.2571 | +28% |

Student's t test:

NS = Not Significant;

* = p < 0.05;

*** = p < 0.001

(−)-Humulone (50, 100 and 200 mg/kg), administered orally 24 hours, 5 hours and 60 minutes before the test, increased the time spent in light compartment in a manner inversely related to the dose, as compared with vehicle control (+48%, +34% and +11%, respectively), significantly so at 50 and 100 mg/kg ($p<0.001$ and $p<0.05$, respectively). It markedly increased the number of crossings at 50 mg/kg, but not at higher doses (+111%, $p<0.001$).

This result together with Example 3 and 4 show that (−)-humulone decreases avoidance of stressful stimuli such as bright light.

Example 5

Preparation of a Soft Gelatin Capsule

A soft gelatin capsule (500 mg) is prepared comprising the following ingredients:

| Ingredient | Amount per Capsule |
| --- | --- |
| (−)-Humulone | 200 mg |
| Lecithin | 50 mg |
| Soy bean oil | 250 mg |

Two capsules per day for 3 months may be administered to a human adult for the reduction of tension, irritability, discontent and unhappiness under stressful conditions at work or life events.

For normalization of symptoms associated with disturbances of circadian rhythm such as jet lag due to long distance flights, two capsules are taken in the morning and evening one day before, during the flight, and at least one week thereafter.

Chronic shift workers take one capsule per day during night shift phases.

Example 6

Preparation of a Tablet

A 400 mg-tablet is prepared comprising the following ingredients:

| Ingredient | Amount per tablet |
| --- | --- |
| (−)-Humulone | 100 mg |
| Green Tea Extract, e.g. TEAVIGO ® from DSM Nutritional Products, Kaiseraugst, Switzerland | 150 mg |

For general well being, energizing and stress alleviation, as well as for reduction of irritability and general maintenance of relaxed attitude upon a hectic life style one tablet may be taken twice daily for 3 months.

Example 7

Preparation of an Instant Flavoured Soft Drink

| Ingredient | Amount [g] |
| --- | --- |
| (−)-Humulone | 0.9 |
| Sucrose, fine powder | 922.7 |
| Ascorbic acid, fine powder | 2.0 |
| Citric acid anhydrous powder | 55.0 |
| Lemon flavour | 8.0 |
| Trisodium citrate anhydrous powder | 6.0 |
| Tricalciumphosphate | 5.0 |
| β-Carotene 1% CWS from DNP AG, Kaiseraugst, Switzerland | 0.4 |
| Total amount | 1000 |

All ingredients are blended and sieved through a 500 µm sieve. The resulting powder is put in an appropriate container and mixed on a turbular blender for at least 20 minutes. For preparing the drink, 125 g of the obtained mixed powder are taken and filled up with water to one liter of beverage.

The ready-to-drink soft drink contains ca. 30 mg (−)-humulone per serving (250 ml). As a strenghtener and for general well being 2 servings per day (240 ml) should be drunk.

Example 8

Preparation of a Fortified Non Baked Cereal Bar

| Ingredient | Amount [g] |
| --- | --- |
| (−)-Humulone | 0.95 |
| Sugar | 114.55 |
| Water | 54.0 |
| Salt | 1.5 |
| Glucose syrup | 130.0 |
| Invert sugar syrup | 95.0 |
| Sorbitol Syrup | 35.0 |
| Palmkernel fat | 60.0 |
| Baking fat | 40.0 |
| Lecithin | 1.5 |
| Hardenend palm-oil | 2.5 |
| Dried and cut apple | 63.0 |
| Cornflakes | 100.0 |
| Rice crispies | 120.0 |
| Wheat crispies | 90.0 |
| Roasted hazelnut | 40.0 |
| Skim milk powder | 45.0 |
| Apple flavour 74863-33 | 2.0 |
| Citric acid | 5.0 |
| Total amount | 1000 |

(−)-Humulone is premixed with skim milk powder and placed in a planetary bowl mixer. Cornflakes and rice crispies are added and the total is mixed gently. Then the dried and cut apples are added. In a first cooking pot sugar, water and salt are mixed in the amounts given above (solution 1). In a second cooking pot glucose, invert and sorbitol syrup are mixed in the amounts given above (solution 2). A mixture of baking fat, palmkernel fat, lecithin and emulsifier is the fat phase. Solution 1 is heated to 110° C. Solution 2 is heated to 113° C. and then cooled in a cold water bath. Afterwards solution 1 and 2 are combined. The fat phase is melted at 75° C. in a water bath. The fat phase is added to the combined mixture of solution 1 and 2. Apple flavour and citric acid are added to the liquid sugar-fat mix. The liquid mass is added to the dry ingredients and mixed well in the planetary bowl mixer. The mass is put on a marble plate and rolled to the desired thickness. The mass is cooled down to room temperature and cut into pieces. The non baked cereal bar contains ca. 25 mg (−)-humulone per serving (30 g). For general wellbeing and energizing 1-2 cereal bars should be eaten per day.

Example 9

Dry Dog Feed Comprising Humulone for Relieving Stress and Revitalizing the Dog

Commercial basal diet for dogs (e.g. Mera Dog "Brocken", MERA-Tiernahrung GmbH, Marienstraβc 80-84, D-47625 Kevelaer-Wetten, Germany) is sprayed with a solution of humulone in water containing suitable stabilizers (i.e. rosemary extract containing carnosic acid and carnosol) and antioxidants such as vitamin C (e.g. ROVIMIX® C-EC from DSM Nutritional Products Ltd, Kaiseraugst, Switzerland) and its derivatives, i.e. Natrium-ascorbyl mono-phosphate (e.g. STAY-C® 50 from DSM Nutritional Products Ltd, Kaiseraugst, Switzerland) or a mixture of tri-, di- and monophosphate esters of sodium/calcium L-ascorbate (e.g. ROVIMIX® STAY-C® 35 from DSM Nutritional Products Ltd, Kaiseraugst, Switzerland) in an amount sufficient to administer to a dog a daily dose of 50 mg humulone per kg body weight. The food composition is dried to contain dry matter of about 90% by weight. For an average dog of 10 kg body weight to consume approx. 200 g dry feed per day, the dog food contains approx. 2500 mg humulone/kg food. For heavier dogs, the feed mix is prepared accordingly. For reduction of stress, fear and aggressiveness in dogs, the food can be given to dogs in animal shelter farms on a regular basis. Before veterinarian visits or stays in veterinarian clinics or holiday separation, the food is given at least on week before, during the stressful event and one week thereafter.

Example 10

Wet Cat Food Comprising Humulone

Commercial basal diet for cats (e.g. Happy Cat "Adult", Tierfeinnahrung, Südliche Hauptstraβe 38, D-86517 Wehringen, Germany) is mixed with a solution of humulone in water containing suitable stabilizers (i.e. rosemary extract containing carnosic acid and carnosol) and antioxidants such as vitamin C (e.g. ROVIMIX® C-EC from DSM Nutritional Products Ltd, Kaiseraugst, Switzerland) and its derivatives, i.e. Natrium-ascorbyl mono-phophat (e.g. STAY-C® 50 from DSM Nutritional Products Ltd, Kaiseraugst, Switzerland) or a mixture of tri-, di- and monophosphate esters of sodium/calcium L-ascorbate (e.g. ROVIMIX® STAY-C® 35 from DSM Nutritional Products Ltd, Kaiseraugst, Switzerland) in an amount sufficient to administer to a cat a daily dose of 100 mg humulone per kg body weight. For an average cat of 5 kg of body weight to consume approx. 400 g of wet food, the cat food contains 1250 mg/kg. The food composition is dried to contain dry matter of about 90% by weight. For reduction of stress, fear and aggressiveness in cats, the food can be given to cats in animal shelter farms on a regular basis. Before veterinarian visits or stays in veterinarian clinics, the food is given at least on week before, during the stressful event and one week thereafter.

Example 11

Dog Treats Containing Humulone

Commercial dog treats (e.g. Mera Dog "Biscuit" for dogs as supplied by Mera Tiernahrung GmbH, Marienstrasse 80-84, 47625 Kevelaer-Wetten, Germany) are sprayed with a solution of humulone in water containing suitable stabilizers (i.e. rosemary extract containing carnosic acid and carnosol) and antioxidants such as vitamin C (e.g. ROVIMIX® C-EC from DSM Nutritional Products Ltd, Kaiseraugst, Switzerland) and its derivatives, i.e. Natrium-ascorbyl mono-phosphat (e.g. STAY-C® 50 from DSM Nutritional Products Ltd, Kaiseraugst, Switzerland) or a mixture of tri-, di- and monophosphate esters of sodium/calcium L-ascorbate (e.g. ROVIMIX® STAY-C® 35 from DSM Nutritional Products Ltd, Kaiseraugst, Switzerland) in an amount sufficient to administer to the treats 5-50 mg humulone per g treats. The food composition is dried to contain dry matter of about 90% by weight. To reduce fear and tension, the treat can be given during the day in addition to the food, or when feeding is not warranted, i.e. upon travels, for up to 5 times daily.

Example 12

Cat Treats Containing Humulone

Commercial cat treats (e.g. Whiskas Dentabits for cats as supplied by Whiskas, Master-foods GmbH, Eitzer Str. 215, 27283 Verden/Aller, Germany) are sprayed with a solution of humulone in water containing suitable stabilizers (i.e. rosemary extract containing carnosic acid and carnosol) and antioxidants such as vitamin C (e.g. ROVIMIX® C-EC from DSM Nutritional Products Ltd, Kaiseraugst, Switzerland) and its derivatives, i.e. Natrium-ascorbyl mono-phophat (e.g. STAY-C® 50 from DSM Nutritional Products Ltd, Kaiseraugst, Switzerland) or a mixture of tri-, di- and monophosphate esters of sodium/calcium L-ascorbate (e.g. ROVIMIX® STAY-C® 35 from DSM Nutritional Products Ltd, Kaiseraugst, Switzerland) in an amount sufficient to administer to the treats 5-50 mg humulone per g treats. The food composition is dried to contain dry matter of about 90% by weight. To reduce fear and tension, the treat can be given during the day in addition to the food, or when feeding is not warranted, i.e. upon travels, for up to 5 times daily.

Example 13

Reduction of Stress in Poultry (Chicken, Broiler, Laying Hens, Turkey, Quails, Ducks, Geese)

Humulone is dissolved in the drinking water containing suitable stabilizers (i.e. rosemary extract containing carnosic acid and carnosol) and antioxidants such as vitamin C (e.g. ROVIMIX® C-EC from DSM Nutritional Products Ltd, Kaiseraugst, Switzerland) and its derivatives, i.e. Natrium-ascorbyl mono-phophat (e.g. STAY-C®) 50 from DSM Nutritional Products Ltd, Kaiseraugst, Switzerland) or a mixture of tri-, di- and monophosphate esters of sodium/calcium L-ascorbate (e.g. ROVIMIX® STAY-C® 35 from DSM Nutritional Products Ltd, Kaiseraugst, Switzerland) at a concentration of 2 g/kg water, with an average drinking volume of 100 ml per day, each chicken, broiler, laying hen (average weight 1-1.5 kg) is provided with 200-250 mg/kg/d. Amounts are adapted for body weight of heavier species and according to the development of body weight.

To prevent losses in egg production, feather picking and cannibalism, poultry is provided regularly with drinking water containing humulone until slaughter. For reduction of stress upon transport, poultry receives the product in the drinking water at least 1-3 days before transport.

Example 14

Reduction of Transport Stress in Cattle and Swine

Humulone is dissolved in the drinking water containing suitable stabilizers (i.e. rosemary extract containing carnosic acid and carnosol) and antioxidants such as vitamin C (e.g. ROVIMIX® C-EC from DSM Nutritional Products Ltd, Kaiseraugst, Switzerland) and its derivatives, i.e. Natrium-ascorbyl mono-phophat (e.g. STAY-C® 50 from DSM Nutritional Products Ltd, Kaiseraugst, Switzerland) or a mixture of tri-, di- and monophosphate esters of sodium/calcium L-ascorbate (e.g. ROVIMIX® STAY-C® 35 from DSM Nutritional Products Ltd, Kaiseraugst, Switzerland) at a concentration of 1.4 g/kg water with an average drinking volume of 20 L per day for swine, the dose for a pig (average weight at slaughter up to 140 kg) is 200 mg/kg/d. For cattle (average weight 800 kg) the amount in drinking water is 1.6 g/kg water, assuming a drinking volume of 100 L/d. To prevent stress during transport and quality loss of meat, the animals are treated at least 3 days before and during transport until slaughter.

The invention claimed is:

1. A method of relieving stress in pets or farm animals in need thereof comprising administering a stress reducing amount of lupulone.

2. A method according to claim 1, wherein the animals are selected from the group consisting of cats, dogs, poultry, cattle, swine, goats, sheep, minks, foxes and hares.

3. A method according to claim 1, wherein the animals are subject to a stressful condition selected form the group consisting of separation, change or loss of the owner, holiday separation, husbandry in so-called "animal hotels", husbandry in animal shelters, dense husbandry and breeding.

4. A method according to claim 1, wherein the lupulone is present in fortified food, in fortified feed, in fortified beverages or in dietary supplements.

* * * * *